(12) United States Patent
Childers et al.

(10) Patent No.: US 6,894,053 B2
(45) Date of Patent: May 17, 2005

(54) SEROTONERGIC AGENTS WITH LONG-ACTING IN VIVO EFFECTS

(75) Inventors: Wayne E. Childers, New Hope, PA (US); Michael G. Kelly, Thousand Oaks, CA (US); Lee E. Schechter, Toms River, NJ (US); Sharon J. Rosenzweig-Lipson, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/734,882

(22) Filed: Dec. 12, 2003

(65) Prior Publication Data

US 2004/0127505 A1 Jul. 1, 2004

Related U.S. Application Data

(62) Division of application No. 10/114,577, filed on Apr. 2, 2002, now Pat. No. 6,696,450.
(60) Provisional application No. 60/281,542, filed on Apr. 4, 2001.

(51) Int. Cl.[7] ...................... A61K 31/495; A61P 25/18; A61P 25/32; A61P 13/02
(52) U.S. Cl. ................... 514/255.03; 544/393
(58) Field of Search ...................... 514/255.03

(56) References Cited

U.S. PATENT DOCUMENTS

| | | | |
|---|---|---|---|
| 4,873,331 A | 10/1989 | Childers et al. | |
| 4,882,432 A | 11/1989 | Abou-Gharbia et al. | |
| 4,988,814 A | 1/1991 | Abou-Gharbia et al. | |
| 5,340,812 A | 8/1994 | Cliffe | |
| 5,486,518 A | 1/1996 | Yardley et al. | |
| 5,519,025 A | 5/1996 | Yardley et al. | |
| 6,376,494 B1 | 4/2002 | Childers et al. | |

FOREIGN PATENT DOCUMENTS

| | | |
|---|---|---|
| EP | 0 395 313 A2 | 12/1999 |
| WO | WO 99/65887 | 12/1999 |
| WO | WO 00/52002 | 9/2000 |

OTHER PUBLICATIONS

Victor W. Pike et al., Med. Chem. Res., 1995, 208, 5.
Gunter Engel et al., Naunyn–Schmiedeberg's Arch. Pharmacol., 1984, 328–336, 325.
Gunter Engel et al., Naunyn–Schmiedeberg's Arch. Pharmacol., 1981, 277–285, 317.
Derek T. Chalmers et al., TiPS, Apr. 1996, 166–179, 17.

Primary Examiner—Richard L. Raymond
Assistant Examiner—Kahsay Habte
(74) Attorney, Agent, or Firm—Rebecca R. Barrett

(57) ABSTRACT

Compounds of the formula

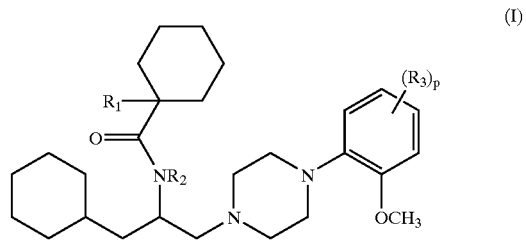

(I)

have a long duration of action and are useful for the treatment of chronic diseases resulting from the dysfunction of the serotonergic 5-$HT_{1A}$ system, such as schizophrenia and other psychotic disorders such as paranoia and manodepressive illness.

4 Claims, No Drawings

SEROTONERGIC AGENTS WITH LONG-ACTING IN VIVO EFFECTS

This application is a divisional of application Ser. No. 10/114,577, filed on Apr. 2, 2002, now U.S. Pat. No. 6,646,450, which claims priority from provisional application Ser. No. 60/281,542, filed on Apr. 4, 2001, the entire disclosure of which is hereby incorporated by reference.

This invention relates to serotonergic agents with long-acting in vivo effects, to processes for preparing them, methods of treatment using them and pharmaceutical compositions containing them.

BACKGROUND OF THE INVENTION

Treatment of disorders such as schizophrenia and Alzheimer's disease and other chronic CNS conditions are problematic in that strict compliance is important and often requires the aid of a caretaker. Ways of increasing compliance which would aid the patient and caretakers and are greatly desirable.

WO 99/65887 discloses compounds of the broad genus of formula A:

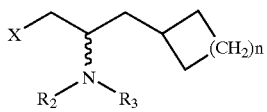

which include compounds where:

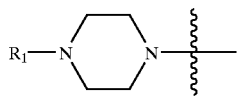

X is
n is 3;
$R_1$ is $C_6$–$C_{10}$-aryl, $R_2$ is selected from the group consisting of H and $C_1$–$C_6$ alkyl; $R_3$ is $COR_5$, and $R_5$ is $C_3$–$C_6$ cycloalkyl, the optical isomers; and the pharmaceutically acceptable salts thereof.

Said compounds are taught to be useful in the treatment of anxiety, depression, schizophrenia, cognitive deficits, nausea and vomiting, and in the treatment of prostate cancer.

DESCRIPTION OF THE INVENTION

Applicants have found that certain compounds of the general formula I:

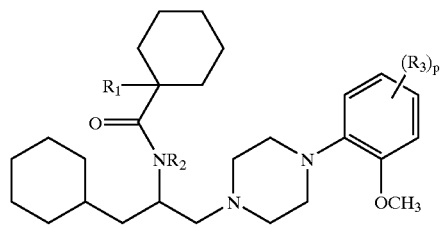

wherein
$R_1$=H or lower alkyl of 1–4 carbon atoms,
$R_2$=H or lower alkyl or 1–4 carbon atoms;
$R_3$ is I and p is 0 or 1, and their pharmaceutically acceptable acid addition salts, display an unexpectedly long duration of action in vivo, making them particularly useful as 5-$HT_{1A}$ antagonists in the treatment of chronic diseases resulting from the dysfunction of the serotonergic 5-$HT_{1A}$ system.

Preferred compounds are those of the general formula I where:
$R_1$=H or $CH_3$ and $R_2$=H or $CH_3$; and pharmaceutically acceptable acid addition salts thereof. The most preferred compounds of general formula I are 1-Methyl-cyclohexanecarboxylic acid {(1R)-1-cyclohexylmethyl-2-[4-(2-methoxyphenyl)-piperazin-1-yl]-ethyl}-amide

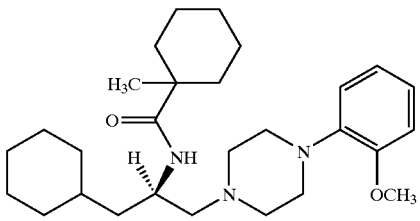

and the pharmaceutically acceptable acid addition salts thereof.

The compounds of formula I contain an asymmetric carbon atom and may exist in different stereoisomeric forms, e.g. as a racemate or as optically active forms. The present invention encompasses the pure stereoisomers as well as racemates of Formula I.

Compounds of Formula I are useful for the treatment of chronic diseases resulting from the dysfunction of the serotonergic 5-$HT_{1A}$ system. With half-lives measured by days rather than hours, compounds of the present invention may be admininstered less frequently and are expected to be particularly useful for the treatment of conditions where compliance is traditionally problematic. A therapeutically effective dose of compounds of Formula I may be provided to a patient as infrequently as once during a seven day period. Dosing may be no more than once during a ten day period in some embodiments of the invention, and as infrequently as once every fourteen days in still other embodiments of the invention.

Compounds of the present invention may be administered to a patient suffering from chronic central nervous system disorders related to or caused by dysfuntion of the serotonergic 5-$HT_{1A}$ system, such as schizophrenia and other psychotic disorders such as paranoia and mano-depressive illness.

Similarly, the treatment of cognitive disorders with compounds having very long lasting effects would be particularly useful. For instance, treatment of cognitive deficits associated with Alzheimer's disease and other dementias with a compound requiring less frequent dosing would improve compliance with such patients. Thus, compounds of the present invention may be useful for the treatment of cognitive disorders associated with mild cognitive impairment (MCI), Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

Anxiety (generalized anxiety disorder, panic attacks and obsessive compulsive disorder) may similarly be treated with compounds of the present invention having long duration of action.

Another condition where compliance is problematic and where compounds of the present invention are expected to have particular value is the treatment of alcohol and drug withdrawal, including nicotine withdrawal.

In addition, conditions where symptoms are exhibited in a chronic manner would be particularly amenable to treatment with compounds of the present invention. For example, chronic pain, motor disorders such as Parkinson's disease, and Tourette's syndrome could be treated with compounds of the present invention.

Other conditions where treatment with compounds having long duration of action may be advantageous are autism, attention deficit disorder, hyperactivity disorders, stroke, treatment of eating disorders such as obesity, anorexia, and bulimia, sexual dysfunction, sleep disorders, social phobias, thermoregulatory disorders, endocrine disorders, urinary incontinence, vasospasm and prostate cancer.

Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses by potentiating inhibitors of serotonin reuptake such as SSRIs and SNRIs, including, but not limited to fluoxetine, venlafaxine, duloxetine, sertraline, paroxetine, fluvoxamine, nefazodone, and mirtazapine. Potentiating, as used herein refers to providing increased availability of serotonin compared the usual increase observed with administration of an inhibitor of serotonin reuptake alone, optionally with a more rapid onset of action. Thus compounds of the present invention may be provided no more than once during a seven day period in combination with a second component which is an inhibitor of serotonin reuptake.

The long-lasting effects of the compounds of this invention also make them useful as biological tools to study the role and effects of functional 5-HT$_{1A}$ antagonism in vivo and in vitro. The application of the long-lasting in vitro and in vivo effects of the compounds of this invention includes the use of the compounds of this invention labeled with isotopes of the naturally occurring elements within the structures of the compounds, e.g. radioactive isotopes or isotopically enhanced. Uses include, but are not limited to, use of the labeled compounds as radioligands for binding studies, use of the labeled compounds as radioligands for in vitro and in vivo imaging a population of cells, and use of the labeled compounds for positron emission topography (PET) studies in mammals including, but not limited to mouse, cats, dogs, monkeys and humans. The compounds would also have tremendous value as biological agents that are able to induce long-term blockade of the 5-HT$_{1A}$ receptor after an acute administration. The consequences of this can be studied in cellular preparations and in young and adult animals. These studies may be multidisciplinary and can investigate many parameters associated with, but not limited to, physiology, biochemistry, behavior and anatomy. This would allow investigations to examine the functional role of the 5-HT$_{1A}$ receptor in the brain as a whole after systemic injections or in discrete brain regions after intracerebral injections. This would have tremendous advantage over molecular biological manipulations such as knockout or transgenic animals and antisense technologies which are more challenging from a technical standpoint and require more time to achieve.

The compounds of the present invention can be prepared by conventional chemical methods which are well known to those skilled in the art of chemistry using chemicals that are either commercially available or readily prepared following standard literature procedures. For example, the compounds may be prepared by the general methods disclosed in WO 99/65887. Such disclosed methods include acylating an amine of formula III (where R$_2$ is defined above) with an acylating agent of formula IV, where R$_1$ is defined above (Scheme 1). Examples of acylating derivatives include but are not limited to acid halides (e.g., acid chloride), anhydrides and activated esters and amides.

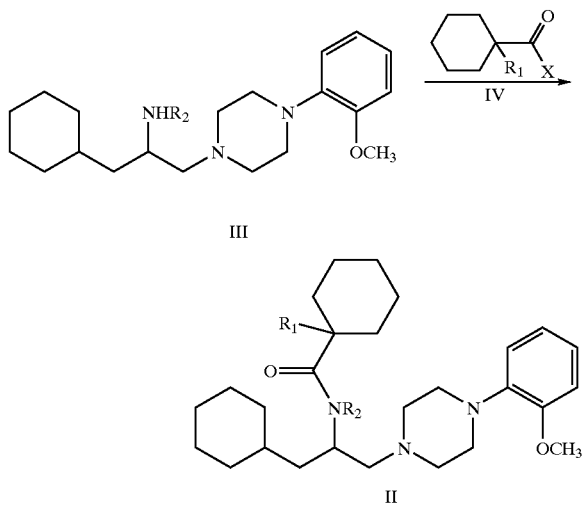

Scheme 1

The starting materials of general formula III may be provided by the general route disclosed in WO 99/65887 and specifically by the exemplified route described WO 99/65887.

Isotopes may be introduced into the structures of the compounds of the present invention using literature methods and standard chemical methods that are well known to those skilled in the art of chemistry. Isotopes for labeling the compounds of this invention include, but are not limited to, $^2$H, $^3$H, $^{11}$C, $^{13}$C, $^{14}$C, $^{125}$I and $^{131}$I. Preferably, compounds of the invention are labeled with $^3$H, $^{11}$C, or $^{14}$C. For example, a precursor of the compound may be reacted with isotope containing reagent such that the isotope is incorporated into the resulting molecule. For example, a phenolic precursor of a compound of the invention may be alkylated with a labeled alkylating agent such as [$^3$H]methyl iodide or [$^{11}$C]methyl iodide to provide compound containing a labeled methoxy-substituted phenyl group, using the methodology described by Pike et al. (*Med. Chem. Res.* (1995), 5: 208). The phenolic precursor VI can be obtained by demethylation of the amine of formula III to give intermediate V (Scheme 2). Acylation of compound V gives the phenolic intermediate VI, which can be treated with methyl iodide containing an isotope ($^2$H, $^3$H, $^{11}$C, $^{13}$C, $^{14}$C) to yield the final labeled product II.

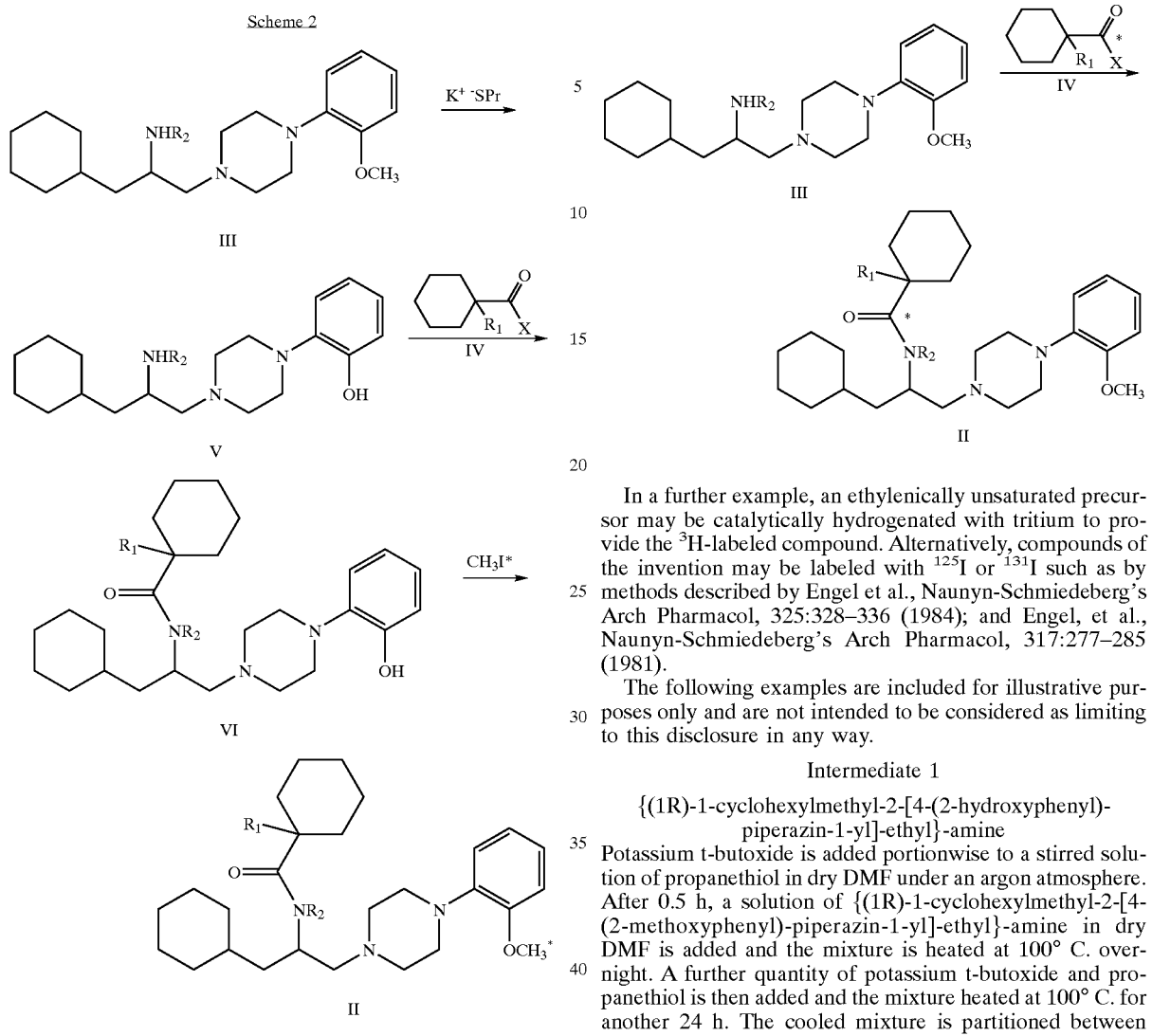

Throughout the schemes, labels are denoted with a "*".

Carbon labels ($^{11}C$, $^{13}C$, $^{14}C$) may also be introduced into the carbonyl moiety of the structures of the present invention according to the general methodology described by Pike et al. by treating the Grignard derivative of an appropriate cyclohexyl halide with labeled carbon dioxide to form labeled formula IV, which can then be used to acylate intermediate III, as shown in Scheme 3.

Scheme 3

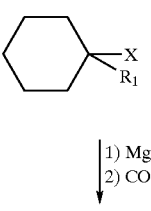

In a further example, an ethylenically unsaturated precursor may be catalytically hydrogenated with tritium to provide the $^3H$-labeled compound. Alternatively, compounds of the invention may be labeled with $^{125}I$ or $^{131}I$ such as by methods described by Engel et al., Naunyn-Schmiedeberg's Arch Pharmacol, 325:328–336 (1984); and Engel, et al., Naunyn-Schmiedeberg's Arch Pharmacol, 317:277–285 (1981).

The following examples are included for illustrative purposes only and are not intended to be considered as limiting to this disclosure in any way.

Intermediate 1

{(1R)-1-cyclohexylmethyl-2-[4-(2-hydroxyphenyl)-piperazin-1-yl]-ethyl}-amine

Potassium t-butoxide is added portionwise to a stirred solution of propanethiol in dry DMF under an argon atmosphere. After 0.5 h, a solution of {(1R)-1-cyclohexylmethyl-2-[4-(2-methoxyphenyl)-piperazin-1-yl]-ethyl}-amine in dry DMF is added and the mixture is heated at 100° C. overnight. A further quantity of potassium t-butoxide and propanethiol is then added and the mixture heated at 100° C. for another 24 h. The cooled mixture is partitioned between water and ethyl acetate. The combined organic layers are washed with brine, dried and concentrated on a rotary evaporator to yield the desired product, which is purified by chromatography on alumina.

Intermediate 2

1-Methyl-cyclohexanecarboxylic acid {(1R)-1-cyclohexylmethyl-2-[4-(2-hydroxy-phenyl)-Piperazin-1-yl]-ethyl}-amide A solution of 1-methylcyclohexanecarbonyl chloride, triethylamine and {(1R)-1-cyclohexylmethyl-2-[4-(2-hydroxyphenyl)-piperazin-1-yl]-ethyl}-amine is stirred at 0° C. under a nitrogen atmosphere for 1 hour. The mixture is then concentrated on a rotary evaporator and partitioned between ethyl acetate and saturated aqueous $NaHCO_3$. The combined organic layers are washed with brine, dried and concentrated on a rotary evaporator to yield the desired product, which is purified by chromatography on alumina.

EXAMPLE 1

1-Methyl-cyclohexanecarboxylic acid {(1R)-1-cyclohexylmethyl-2-[4-(2-methoxyphenyl)-piperazin-1-yl]-ethyl}-amide hydrochloride hydrate To a solution of 0.30 g (0.91 mmol) of {(1R)-1-cyclohexylmethyl-2-[4-(2-methoxyphenyl)-piperazin-1-yl]- ethyl}-amine and 0.25 mL (1.74 mmol) of triethyl-amine in 10 mL of dichloromethane at 0° C. was added dropwise 0.16 g (1.00 mmol) of 1-methylcyclohexane-carboxylic acid chloride in 4 mL of dichloromethane. The reaction mixture was allowed to stir under nitrogen at 0° C. for one hour, and was then concentrated on a rotary evaporator, diluted with ethyl acetate and washed with saturated aqueous $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to the hydrochloride·hydrate salt of the title compound with ethanolic HCl to yield 0.30 g (63%) of a light yellow solid; mp=119–121° C.; MS (+) ESI m/z=456 (M+H)$^+$.

Analysis for $C_{28}H_{45}N_3O_2 \cdot HCl \cdot H_2O$ Calculated: C: 65.92; H: 9.48; N: 8.24 Found: C: 65.85; H: 9.26; N: 7.67.

EXAMPLE 2

[Methoxy-$^3$H]1-1-Methyl-cyclohexanecarboxylic acid {(1R)-1-cyclohexylmethyl-2-[4-(2-methoxyphenyl)-piperazin-1-yl]-ethyl}-amide hydrochloride hydrate Sodium hydride is added to a solution of 1-Methyl-cyclohexanecarboxylic acid {(1R)-1-cyclohexylmethyl-2-[4-(2-hydroxyphenyl)-piperazin-1-yl]-ethyl}-amide in DMF and the solution is stirred at room temperature under nitrogen for 2 hours. [$^3$H] methyl iodide is added to the reaction mixture which is stirred at room temperature for 1.5 hours. The reaction mixture is pumped to dryness on the manifold and taken to dryness several times with ethanol.

EXAMPLE 3

[Methoxy-$^{11}$C] 1-Methyl-cyclohexanecarboxylic acid }(1R)-1-cyclohexylmethyl-2-[4-(2-methoxyphenyl)-piperazin-1-yl]-ethyl}-amide hydrochloride hydrate In a suitable manifold, sodium hydride is added to a solution of 1-Methyl-cyclohexanecarboxylic acid {(1R)-1-cyclohexylmethyl-2-[4-(2-hydroxy-phenyl)-piperazin-1-yl]-ethyl}-amide in dimethylformamide under nitrogen. [$^{11}$C]-methyl iodide is distilled into the reaction mixture and the reaction is heated to 80° C. for 5 minutes. After purification by HPLC the material is formulated for i.v. injection by dissolution in normal saline and sterile millipore filtration.

EXAMPLE 4

In Vitro Data

Affinity for the serotonin 5-HT$_{1A}$ receptor was established by assaying the test compound's ability to displace [$^3$H]-8-OH-DPAT from its binding site on the receptor complex in CHO cells stably transfected with the human 5-HT$_{1A}$ receptor following the procedure described by J. Dunlop, Y. Zhang, D. Smith and L. Schechter (J. Pharmacol. Toxicol. Methods, 40, 47–55 (1998)). The compounds of this invention displayed high affinity for the 5-HT$_{1A}$ receptor, as exemplified by the data given for Example 1 in Table 1.

The compounds of this invention displayed 5-HT$_{1A}$ antagonist activity, as measured by the test compound's ability to antagonize the ability of [$^3$H]-8-OH-DPAT to inhibit forskolin-stimulated cAMP turnover in CHO cells stably transfected with the human 5-HT$_{1A}$ receptor following the procedure described by J. Dunlop, Y. Zhang, D. Smith and L. Schechter (J. Pharmacol. Toxicol. Methods, 40, 47–55 (1998)). Data for Example 1 are given in Table 1.

TABLE 1

| Example | 5-HT$_{1A}$ Affinity (IC$_{50}$) | Antagonist Activity cAMP (IC$_{50}$) |
|---|---|---|
| Example 1 | 1.23 nM | 14.6 nM |

EXAMPLE 5

Ex Vivo Data: Long-Lasting Receptor Occupancy

The serotonergic 5-HT$_{1A}$ receptor occupancy in vivo of the compounds of this invention was determined using ex vivo binding techniques. Rats were injected with a 3 mg/kg ip dose of Example 1 or vehicle and then sacrificed after 1, 24, 72, 168, and 336 hours. The brains were dissected and the cortex and hippocampus removed. Tissue was prepared by homogenization and washed once with buffer. Serotonergic 5-HT$_{1A}$ receptors were measured in the membrane preparation using the standard 5-HT$_{1A}$ receptor antagonist [$^3$H]-WAY-100635 (85 Ci/mmol). Specific binding was determined in the presence of 10 mM methiothepin. The ability of the test compounds to displace [$^3$H]-WAY-100635 from the 5-HT$_{1A}$ receptor was then determined and expressed as the fmol/mg protein of [$^3$H]-WAY-100635 remaining in the membrane preparation after treatment with the test compound. Data for Example 1 are shown in Table 2.

It is apparent from the data shown in Table 2 that the compounds of this invention exhibit an unexpectedly long receptor occupancy time. For example, a single administration of the compound of Example 1 is able to significantly inhibit binding of the standard 5-HT$_{1A}$ receptor antagonist WAY-100635 for up to 14 days following administration. This surprisingly long duration of action makes the compounds of this invention useful for the treatment of chronic diseases such as those described above. This surprisingly long duration of action also makes the compounds of this invention useful as a biological tool for the study of the role and effects of 5-HT$_{1A}$ antagonism both in vitro and in vivo.

TABLE 2

| | fmol/mg protein | | | | | | | | | |
|---|---|---|---|---|---|---|---|---|---|---|
| | 1 hour | | 24 hour | | 72 hours | | 7 days | | 14 days | |
| | cortex | striat. | cortex | striat. | cortex | striat. | cortex | striat. | cortex | striat. |
| Vehicle | 13.0 ± 1.0 | 25.0 ± 1.3 | 15.0 ± 0.9 | 25.0 ± 1.9 | 15.0 ± 1.0 | 33.0 ± 3.0 | 17.0 ± 1.9 | 27.0 ± 1.0 | 13.0 ± 0.9 | 22.0 ± 0.7 |
| EX. 1 | 4.0 ± 0.1 | 6.0 ± 0.3 | 8.0 ± 0.6 | 12.0 ± 2.7 | 9.0 ± 0.6 | 14.0 ± 2.3 | 7.0 ± 0.3 | 15.0 ± 1.7 | 11.0 ± 0.3 | 26.0 ± 0.6 |

EXAMPLE 6

In Vivo Data

The ability of the compounds of this invention to function in vivo as $5\text{-HT}_{1A}$ antagonists was assessed in rats using a Fixed Responding Model (Blackman, D., in, "Operant Conditioning: An Experimental Analysis of Behavior", J. Butcher, Ed., Methuen and Co., Ltd., London). In this model rats are trained to respond (lever pressing) under a fixed-ratio 30 schedule of food presentation in order to receive a food pellet reinforcer. Administration of the $5\text{-HT}_{1A}$ agonist 8-OH-DPAT reduces the response rate observed from administration of vehicle (Table 3). $5\text{-HT}_{1A}$ antagonist activity is assessed by determining the test compound's ability to antagonize this decrease in response rate induced by administration of the agonist. As can be seen from Table 3, a 3 mg/kg sc dose of the compound of example 1 completely reverses the effect of a 1 mg/kg sc dose of the $5\text{-HT}_{1A}$ agonist 8-OH-DPAT.

TABLE 3

| | Response Rate (responses/second) | |
|---|---|---|
| Vehicle | 8-OH-DPAT (1 mg/kg sc) | 8-OH-DPAT (1 mg/kg sc) + Example 1 (3 mg/kg sc) |
| 2.3 ± 0.5 | 0.5 ± 0.2 | 2.4 ± 0.3 |

EXAMPLE 7

Long-Lasting Functional $5\text{-HT}_{1A}$ Antagonist Effects In Vivo

In corroboration with the ex vivo binding results, the compounds of this invention exhibited a surprisingly long duration of action in vivo as $5\text{-HT}_{1A}$ antagonists. In the Fixed Responding Model, a single dose of Example 1 (3 mg/kg sc) significantly inhibited the decrease in responding obtained by daily administration of a 1 mg/kg sc dose of the $5\text{-HT}_{1A}$ agonist 8-OH-DPAT for up to 17 days post administration (Table 4). This long-lasting effect makes the compounds of this invention especially useful in the treatment of chronic diseases such as those described above. Additionally, the long-lasting effects of the compounds of this invention make them useful as biological tools for the study of the role and effects of $5\text{-HT}_{1A}$ antagonism both in vitro and in vivo.

conventional pharmaceutical carriers. Applicable solid carriers can include one or more substances which may also act as flavoring agents, lubricants, solubilizers, suspending agents, fillers, glidants, compression aids, binders, tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either in liquid or solid composition form. Preferably, the pharmaceutical compositions containing the present compounds are in unit dosage form, e.g., as tablets or capsules. In such form, the composition is sub-divided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a

TABLE 4

| | | | Response Rate (responses/second) | | | | | | |
|---|---|---|---|---|---|---|---|---|---|
| | 8-OH-DPAT 1 mg/kg | | | 8-OH-DPAT (1 mg/kg sc) + Vehicle or Test Compound | | | | | |
| Veh. | sc | | Day 1 | Day 4 | Day 7 | Day 11 | Day 14 | Day 17 | Day 21 |
| 2.3 ± 05 | 0.5 ± 0.2 | Vehicle | 0.7 ± 02 | 0.4 ± 0.1 | 0.6 ± 0.2 | 0.4 ± 0.1 | 0.5 ± 0.2 | 0.5 ± 0.2 | 0.5 ± 0.2 |
| | | Example 1 (3 mg/kg sc) | 2.4 ± 0.3 | 2.1 ± 0.3 | 2.0 ± 0.3 | 1.8 ± 0.2 | 1.7 ± 0.3 | 1.0 ± 0.2 | 0.7 ± 0.2 |

Pharmaceutical Composition

The compounds of the present invention may be administered orally or parentally, neat or in combination with conventional pharmaceutical carriers.

capsule or tablet itself, or it can be the appropriate number of any such compositions in package form. The therapeutically effective dosage to be used in the treatment of a specific psychosis, CNS disorder, motor disorder, alcohol or drug withdrawal, migraine, obesity, or other conditions must be subjectively determined by the attending physician and generally ranges from about 5 mg/day to about 75 mg/day. The variables involved include the specific condition(s) being treated and the size, age and response pattern of the patient.

Compounds of the present invention may be provided in combination with a second component which is an inhibitor of serotonin reuptake. Dosages of such combinations must be subjectively determined by a physician who may be generally guided by conventional dosages of serotonin reuptake inhibitors administered alone. The adjunctive therapy of the present invention is carried out by administration of a compound of the present invention together with a second component in any manner which provides effective levels of the two compounds in the body at the same time. They may be administered together in a single dosage form, or may be administered separately. Because of the long duration of action of compounds of the present invention, potentiation of a serotonin reuptake inhibitor may include a single dose of a compound of the present invention no more than once during a seven day period, and one or more doses of the second component given at equal intervals over the seven day period as determined by the duration of action of said second component.

The present invention may be embodied in other specific forms without departing from the spirit and essential attributes thereof and accordingly, reference should be made to the appended claims, rather than to the foregoing specification, as indicating the scope of the invention.

What is claimed is:

1. A method of potentiating the action of an inhibitor of serotonin reuptake comprising administering to a patient in need thereof in combination with a compound of Formula I

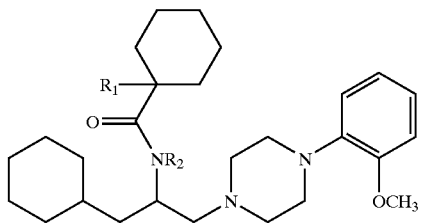

wherein $R_1$=H or lower alkyl of 1–4 carbon atoms, and $R_2$=H or lower alkyl or 1–4 carbon atoms, and pharmaceutical salts thereof, said effective dose being administered no more than once during a seven day periods, in combination with an inhibitor of serotonin reuptake.

2. The method of claim 1 wherein the inhibitor of serotonin reuptake is fluoxetine, venlafaxine, duloxetine, sertraline, paroxetine, fluvoxamine, nefazodone, and mirtazapine.

3. A pharmaceutical composition comprising a compound of Formula I

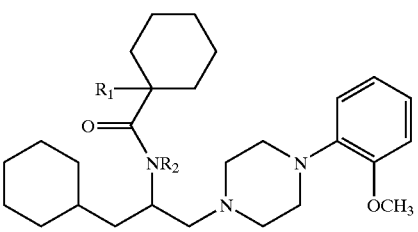

wherein $R_1$=H or lower alkyl of 1–4 carbon atoms, and $R_2$=H or lower alkyl or 1–4 carbon atoms, and pharmaceutical salts thereof, an inhibitor of serotonin reuptake, and a pharmaceutically acceptable carrier or excipient.

4. The composition of claim 3 wherein the inhibitor of serotonin reuptake is fluoxetine, venlafaxine, duloxetine, sertraline, paroxetine, fluvoxamine, nefazodone, and mirtazapine.

* * * * *